United States Patent [19]

Bevan et al.

[11] Patent Number: 5,919,477
[45] Date of Patent: Jul. 6, 1999

[54] TRANSDERMAL SYSTEM FOR SIMULTANEOUS DELIVERY OF A NUMBER OF ACTIVE PRINCIPLES

[75] Inventors: Bruno Bevan, Chevigny Saint Sauveur; Cécile Aillaud, Dijon, both of France

[73] Assignee: Laboratoires D'Hygiene et de Dietetique, Paris, France

[21] Appl. No.: 08/849,688

[22] PCT Filed: Dec. 9, 1995

[86] PCT No.: PCT/FR95/01696

§ 371 Date: Jun. 11, 1997

§ 102(e) Date: Jun. 11, 1997

[87] PCT Pub. No.: WO96/19203

PCT Pub. Date: Jun. 27, 1996

[30] Foreign Application Priority Data

Dec. 21, 1994 [FR] France ................................ 94 15416

[51] Int. Cl.⁶ ........................................... A61F 13/02
[52] U.S. Cl. .................................. 424/448; 424/449
[58] Field of Search ..................... 424/449, 448

[56] References Cited

U.S. PATENT DOCUMENTS 4,666,441  5/1987  Andriola ............................. 604/897
4,911,707  3/1990  Heiber ................................ 424/449
5,064,422  11/1991  Wick .................................. 604/307
5,071,656  12/1991  Lee .................................... 424/448
5,128,137  7/1992  Muller ............................... 424/449
5,350,581  9/1994  Kochinke .......................... 424/443
5,538,736  7/1996  Hoffmann .......................... 424/448

FOREIGN PATENT DOCUMENTS 9406383  6/1990  WIPO .
9006736  3/1994  WIPO .

*Primary Examiner*—D. Gabrielle Brouillette
*Attorney, Agent, or Firm*—Carmen Pili Curtis

[57] ABSTRACT

A novel system for percutaneously delivering at least two active principles, consisting of at least two juxtaposed devices. The system includes (i) a first device containing a mixture of all the active principles in which at least one first active principle (A) is present in an amount enabling the effective therapeutic dose to be delivered, and at least one second active principle (B) is present in an amount smaller than the amount needed to deliver the effective therapeutic dose; and (ii) one or more additional devices each containing a single active principle (B) selected from those in the first device and provided in an amount smaller than the amount needed to deliver the effective therapeutic dose, said additional device(s) being designed to top up the amount of each of the active principles (B) in the system until the effective therapeutic dose is achieved.

20 Claims, No Drawings

TRANSDERMAL SYSTEM FOR SIMULTANEOUS DELIVERY OF A NUMBER OF ACTIVE PRINCIPLES

This Application is a 371 of PCT/FR95/01696, filed Dec. 9, 1995.

FIELD OF THE INVENTION

The present invention relates to systems for the transdermal delivery of a number of active principles simultaneously, said systems being designed so as to facilitate adjustment of the delivered doses of one or more active principles and reduce the surface area of such systems in order to improve safety and comfort when used by the patient.

PRIOR ART

There are numerous devices currently in existence for the transdermal delivery of an active principle.

The composition of these devices is defined for the purpose of (i) ensuring a good physicochemical stability of the active principle over time, and (ii) obtaining an optimal transdermal absorption flux per unit surface area. Thus the dose of active principle delivered in the course of a treatment is mainly determined by the surface area of the device applied to the skin.

Now, this surface area must not be so large as to cause physical discomfort when the device is used and produce a device whose size and esthetic appearance would rule out its use altogether. The device must also have good adhesion and cohesion properties, making it easy, pleasant and discreet to apply when used.

Thus devices containing a single active principle are produced at the present time and satisfy these demands, i.e. they are effective, small and comfortable and neither creep nor become detached during use.

On the other hand, the production of such efficient systems for the delivery of two active principles, or even more than two active principles, still presents numerous problems which become increasingly difficult to solve as the number of active principles to be delivered increases.

A first known technical solution among those envisaged in the prior art involves transdermal systems which consist of a single device containing all the active principles mixed together. Such systems are described for example in patent documents EP-A-0 285 563, WO-A-92/07589, WO-A-92/07590 and WO-A-94/06383. Although these systems have the advantage of being small, they prove generally very complex, if not impossible, to perfect.

In fact, by virtue of their nature and their physicochemical properties, the active principles behave in different ways towards the corneal layer and often have important influences on the composition of the device.

Because the skin has different permeabilities to the active principles, each active principle has a different absorption flux. It therefore proves virtually impossible to obtain the desired therapeutic dose of each active principle to be delivered by simultaneously using the same absorption area and the same formulation.

Furthermore, if it is necessary to readjust the delivered dose of at least one of the active principles during clinical development, it is impossible to modify the delivered dose of this active principle independently of those of the other active principles without having to change the formulation of the other components.

Similarly, it is also common for one and the same system for the transdermal delivery of a number of active principles to be used for delivering several dosages of these active principles according to the patients or pathological conditions treated.

This will be done by choosing different surface areas of said system on account of the fact that the dose of active principle delivered will be proportional to the surface area applied to the skin.

In the case of such a system for the delivery of a number of active principles where different posologies are required, if at least two active principles do not remain in the same dose ratio for all the chosen posologies, or if one active principle is delivered at a fixed dose, it will be impossible to obtain the different desired posologies by varying the surface area of the device, since in this case the doses of each active principle vary simultaneously as a function of the surface area and in constant dose ratios.

In both the above cases, therefore, the benefit of the work already put in is lost and comfortable systems with good fluxes and good physical properties are forsaken.

Now, the choice of components forming part of the formulation of the device becomes very rapidly restricted as the number of active principles increases, the latter often imposing conflicting constraints.

In fact, the active principles may be partially or totally incompatible with certain constituents of the formulation (resins, solvents, plasticizers, polymers, skin absorption promoters, etc.). They may have different solubilities and stability temperatures and some of them recrystallize over time, degrade when applied or can only be used in the composition at concentrations which are too low to obtain the intended therapeutic dosage. Likewise, there is no universal skin absorption promoter for all active principles in order to increase their transdermal fluxes. Therefore, to administer different active principles, it is often necessary to use several promoters or solvents. Now, the introduction of any new substance may cause or raise problems of irritation and the system's cohesion or adhesion.

By the same token, this set of constraints (compatibility, solubility, etc.) also affects the different constituents of the formulation other than the active principles, thereby exacerbating the difficulties of optimizing their role in the formulation and benefiting from the specific advantages they can bring.

In practice, this first technical solution is not workable and leads to an impasse or, at best, to devices hampered by obvious disadvantages for the use of this type of pharmaceutical form.

A second known solution for the simultaneous delivery of a number of active principles consists in producing a system formed of several transdermal devices applied to the skin, each device containing a single active principle. Such systems are described for example in patent documents WO-A-94/06383, WO-A-90/06736 and WO-A-94/13354.

This avoids the above problems of compatibility, stability and adjustment of the desired dosage. Attainment of the desired dose of each active principle is then defined by the surface area of each device.

It is this which constitutes the main disadvantage of this solution, because such a system generally has a large overall surface area, its size increasing with the number of active principles.

Now, in general, the larger a transdermal system is, the more difficult it is to use. This is because it becomes harder to optimize its adhesion and cohesion properties over the whole of the surface area which is to come into contact with the skin.

Thus, the larger the system is, the greater will be the risk of increasing the likelihood of creep of the adhesive mass and hence soiling of the clothes, sensations of pulling, discomfort or even irritation of the skin or cohesive rupture when the system is removed, making the system less manageable and acceptable.

Furthermore, as the dose delivered over time is determined by the surface area of the device applied to the skin, any increase in surface area increases the risk of partial or total detachment of the system or puckering, which can result in a loss of activity because of non-uniform contact with the skin, particularly over curved parts of the body or parts which frequently move.

Similarly, in the case of a reservoir, an inhomogeneous distribution over the whole of the surface area which is to come into contact with the skin necessarily modifies the dose released and does not allow the desired therapeutic activity to be achieved. Thus, in the case of an excessively large reservoir system, where the liquid or semiliquid (solution or gel) containing the active principle tends to stagnate in the lower part of the reservoir under the action of gravity, the surface area utilized will be reduced and the system will ultimately be less effective.

Another disadvantage of a large system, whatever its nature may be, is the risk that it will be poorly accepted by the patient because it is too visible and therefore difficult to conceal.

The esthetic appearance and the discreetness of the transdermal system, possibly combined with a sensation of physical discomfort, are actually important parameters for the acceptability of the product and the patient's compliance with the therapeutic treatment.

All these problems therefore detract from the comfort of the system when in use or, even worse, from its therapeutic efficacy when used by the patient.

The solutions of the prior art are therefore unsatisfactory because they do not succeed in reconciling the possibility of simply adapting the delivered doses of each of the active principles with the production of a system of small overall surface area, allowing safer and more comfortable use when the system is applied to the skin.

OBJECT OF THE INVENTION

In the field of the simultaneous transdermal delivery of a number of active principles, it would therefore be desirable to provide a novel technical solution which enables the desired compromise to be reached without the above-mentioned disadvantages.

It is this object which the present invention proposes to achieve through the production of a system for the simultaneous transdermal delivery of at least two active principles which makes it possible simply to adjust the dose of each active principle to be delivered, while at the same time having a reduced total surface area.

SUBJECT OF THE INVENTION

The above-mentioned object is achieved through the production, as a novel industrial product, of a novel system for the transdermal delivery of at least two active principles which consists of at least two juxtaposed (or associated) devices, said system being characterized in that it comprises (i) a first device containing a mixture of all the active principles in which at least one first active principle (A) is present in an amount which enables the effective therapeutic dose to be delivered, and at least one second active principle (B) is present in an amount which is less than that required to deliver the effective therapeutic dose, and (ii) one or more additional devices each containing a single active principle (B) selected from those present in the first device and provided in an amount which is less than that required to deliver the effective therapeutic dose, said additional device or devices making up the amount of each of the active principles (B) present in the system until the effective therapeutic dose is obtained.

DETAILED DESCRIPTION OF THE INVENTION

The expression "transdermal system" in the present invention denotes the association of at least two devices for the purpose of simultaneously delivering all the active principles by application to the skin.

"Device" is understood here as meaning any system used to deliver at least one active principle transdermally. Such devices are generally classed in two major categories:

reservoir devices, in which the active principle or principles are dissolved in a solvent acting as a vector for transporting the active principle across an adhesive or non-adhesive microporous membrane; and matrix devices, in which the active principle or principles are dissolved or dispersed in a polymer network forming the matrix, which can be self-adhesive or non-adhesive.

These devices can be monolayer or multilayer (also called lamellar), i.e. formed by the superposition of several matrices or reservoirs which may or may not contain one or more active principles, said matrices or reservoirs optionally being separated by microporous membranes.

The association of at least two devices according to the invention can be carried out by techniques known to those skilled in the art, for example by sticking onto a support coated with adhesive, juxtaposed double coating or heat sealing onto a single support. The devices will have a single support in the above cases, but it is also possible to manufacture a system in which each device has an identical or different independent support, association being effected by juxtaposition of the devices, for example by heat sealing, or by associating the devices on an additional support, always by the same techniques.

The support used may be any support generally employed in occlusive or non-occlusive transdermal systems, of variable thickness, which is impermeable to the constituents of the devices.

Preferred supports will be for example in the form of a polyethylene, polypropylene or polyester film, a composite consisting of polyethylene and a vinyl acetate/ethylene copolymer, an aluminized film or else a foam.

In practical terms, the whole of the system or each of the devices may be covered with a protective layer or film which can be peeled off before the system is used, it being possible for said system itself to be packaged in a leaktight protection such as, for example, a polyethylene/aluminum composite.

A device according to the present invention can be made of the materials familiar to those skilled in the art, for example natural or synthetic polymers (such as acrylics or derivatives thereof, silicones, block copolymers, vinyl acetate/ethylene copolymers, rubbers and derivatives thereof, etc.), according to the properties of the active principles to be delivered. Other appropriate known products generally used by those skilled in the art may be associated with said active principles, examples being solubilizing agents, plasticizers, resins, stabilizers, bulking agents or skin permeation promoters.

Likewise, the membranes which may be employed are those generally used in the art in the field of transdermal systems, examples being a film of ethylene/vinyl acetate copolymer.

In the case where one or more matrix devices are used in the system according to the present invention, said matrix devices are manufactured by the coating techniques generally known in the art, either in a solvent phase or by the so-called hot melt technique (i.e. in the absence of a solvent).

Likewise, in the case where devices of the reservoir type are used, said devices are manufactured by the techniques known in the art, an example being creation of the reservoir by heat-sealing the support onto a membrane and simultaneously or non-simultaneously filling the reservoir.

In both cases, in the context of industrial production, the size of the devices is set to the appropriate dimensions, according to the amount of active principle or principles present per unit surface area, to give the chosen doses of active principles to be delivered by the system over a given time.

The transdermal system according to the invention can have any geometric shape: square, rectangular, circular or oval. The different devices can be arranged either side-by-side or concentrically, each device then completely surrounding the previous one, or any other geometric construction can be used. The devices can optionally be separated or surrounded by one or more additional layers, which can be adhesive in order to help hold the unit together if necessary.

Any combination of active principles capable of being applied transdermally and exerting either a topical or a systemic action can be used within the framework of the present invention.

The following possible associations may be mentioned among these combinations:

(a) one or more estrogens with one or more progestins, natural or synthetic, for contraceptive purposes or in the treatment of the symptoms of menopause, for example estradiol, ethynylestradiol, estriol and derivatives thereof in association with norethisterone acetate, norgestrel, levonorgestrel, desogestrel, norgestimate, lynestrenol, gestodene, nomegestrol acetate or dienogest;

(b) β-blocker and diuretic compounds useful especially in cardiovascular diseases, for example timolol, pindolol, bufradol, indenolol or nipradinol in association with amilonide or hydroclothiazide;

(c) corticoid and antihistamine compounds useful especially in the treatment of allergies, for example methylprednisolone, prednisolone, hydrocortisone, beclomethazone or triamcinolone in association with astemizole, dexchlorpheniramine, cetirizine, diphenylhydromine chloride or chloro-pheniramine;

(d) analgesic and anti-inflammatory compounds useful especially in the treatment of pain, for example acetylsalicylic acid, paracetamol or noramidopyrine in association with mefenamic acid, flufenamic acid, diclofenac, oxyphen-butazone, ibuprofen, naxoprene or fenbufene; and (e) antibacterial and antibiotic compounds useful especially in the treatment of infections, for example amoxycillin in association with clavulanic acid, sulfametoxazole in association with trimethoprim, erythromycin in association with acetylsulfafurazole or erythromycin in association with tetracycline.

Advantageously, a system in which the active principles to be delivered simultaneously are chosen on the one hand from estrogen compounds and on the other hand from progestin compounds is particularly recommended.

BEST MODE

The best mode of carrying out the invention consists in using a system for the transdermal delivery of two active principles (A and B), characterized in that it comprises (i) a first matrix device which is a matrix containing in its bulk the active principle A in an amount which enables the effective therapeutic dose to be delivered, and the active principle B in an amount which is less than that necessary to deliver the effective therapeutic dose, and (ii) a second matrix device which is a matrix containing in its bulk the active principle B in an amount which makes up the amount present in said first matrix device until its effective therapeutic dose is obtained.

In other words, a system is recommended which consists of two juxtaposed (or associated) matrices, this system being such that a first matrix which contains a mixture of the two active principles, where one of the two is delivered at a dose which is less than its effective therapeutic dose, is combined with a second matrix which contains this same active principle and which enables its effective therapeutic dose to be delivered.

This system is very useful for the simultaneous delivery of an estrogen and a progestin, in particular for the simultaneous delivery of different doses of 17-β-estradiol, between 25 and 100 μg per 24 hours, and different doses of norethisterone acetate, between 100 and 800 μg per 24 hours, in 17-β-estradiol/norethisterone acetate dose ratios of ¼ to ⅛ respectively, said doses being therapeutically effective in the treatment of the symptoms of menopause and the resulting cardiovascular risks.

The advantages and characteristics of the invention will be understood more clearly from the following description of Examples of systems produced according to the invention and experiments comparing them with systems described in the prior art. Of course, these details taken as a whole do not in any way imply a limitation but are given by way of illustration. The systems according to the invention and the comparative systems are produced by different combinations of the matrix devices described below.

EXAMPLE 1 (device 1)

47.8 g of LEVAPREN® 450P (an ethylene/vinyl acetate copolymer (abbreviated to EVA below) marketed by BAYER), 48 g of crotamiton [N-ethyl-2-N-(2-methylphenyl)-2-butenamide] (marketed by BOEHRINGER INGELHEIM), 0.2 g of IRGANOX® B215 (an antioxidant marketed by CIBA-GEIGY) and 115.53 g of ethyl acetate are placed in a vessel. The mixture is heated for 5 hours until the EVA has completely dissolved. It is stirred at room temperature for 1 hour and 4 g of norethisterone acetate (abbreviated to NETA below), previously dissolved in 20 g of tetrahydrofuran, are then added. The mixture obtained is stirred for about 30 minutes until it is completely homogeneous; it is then left to stand until the bubbles have totally disappeared. The mass obtained is coated onto a siliconized polyester film at room temperature (15–25° C.) to give a deposit of material of (100±10) g/m². The unit obtained is heated at 70° C. for 30 minutes and then transferred to a polyethylene support. The resulting product is then cut to appropriate dimensions. If necessary, the cut products are packaged in sachets, envelopes or leaktight enclosures.

EXAMPLE 2 (device 2)

The procedure is analogous to Example 1 above using 49.8 g of LEVAPREN® 450P, 44 g of crotamiton, 0.2 g of IRGANOX® B215, 116.2 g of ethyl acetate, 2 g of 17-β-estradiol and 4 g of norethisterone acetate (added at the same time as the 17-β-estradiol), these two hormones being dissolved together in 30 g of tetrahydrofuran.

EXAMPLE 3 (device 3)

20.7 g of ELVAX® 46L and 6.9 g of ELVAX® 46 (ethylene/vinyl acetate copolymers marketed by DU PONT) and 6 g of ETHOCEL® (ethyl cellulose marketed by DOW CHEMICAL) are placed in a vessel, with stirring, and heated to about 130° C. 1.2 g of 17-β-estradiol and 18.9 g of EUTANOL® G (2-octyldodecanol marketed by HENKEL) are then incorporated gradually at 130° C., with continued stirring, and the mixture is stirred until it is completely homogeneous. 6.3 g of SURFADONE® LP300 (N-dodecyl-2-pyrrolidone marketed by GAF CORPORATION) are then added at a temperature of the order of 100 to 110° C. and stirring is continued until the mixture is perfectly homogeneous. The mixture obtained is coated, at a temperature between 100 and 140° C., onto an antiadhesive temporary intermediate support, especially a siliconized polyester film, at a rate of (100±10) g/m². The matrix obtained is transferred to a polyethylene support.

EXAMPLE 4 (device 4)

The procedure is identical to Example 3 except that 11 g of ELVAX® 46L, 11 g of ELVAX® 46, 5 g of ETHOCEL®, 15 g of EUTANOL® G, 5 g of SURFADONE® LP300, 1 g of 17-β-estradiol and 2 g of norethisterone acetate are used in this case.

EXAMPLE 5 (device 5)

The procedure is identical to Example 3 except that 33.75 g of ELVAX® 46L, 11.25 g of ELVAX® 46, 10 g of ETHOCEL®, 30.5 g of EUTANOL® G, 4 g of norethisterone acetate and 10.5 g of SURFADONE® LP300 are used in this case.

EXAMPLE 6 (device 6)

13.35 g of KRATON G® 1657 (a poly(styrene/ethylene/butylene/styrene) three-block copolymer marketed by SHELL), 0.1 g of IRGANOX® 565 (an antioxidant marketed by CIBA-GEIGY), 12.5 g of ZONATAC® 105L (a tackifying resin marketed by ARIZONA CHEMICAL), 10.25 g of PARAPOL® 950 (an n-butene/isobutylene copolymer marketed by EXXON CHEMICAL), 10.25 g of EUTANOL® G (2-octyldodecanol marketed by HENKEL), 3 g of SURFADONE® LP300 (N-dodecyl-2-pyrrolidone marketed by GAF CORPORATION) and 25.6 g of cyclohexane are placed in a 250 ml beaker. The mixture is stirred for 6 hours, while being heated at 60° C., until the constituents have completely dissolved. 0.55 g of norethisterone acetate, previously dissolved in 2.75 g of tetrahydrofuran, is then added. The mixture obtained is stirred for 30 minutes until it is completely homogeneous, and then left to stand until the bubbles have totally disappeared. The mixture obtained is coated onto a siliconized polyester film at a rate of (100±10) g/m² at room temperature (15–25° C.). After heating at 70° C. for 0.5 hour, the matrix obtained is transferred to a polyethylene support. The product is then cut to appropriate dimensions and packaged in sachets if necessary.

EXAMPLE 7 (device 7)

13.8 g of VECTOR® 4211D [a poly(styrene/isoprene/styrene) three-block copolymer marketed by EXXON CHEMICAL], 23.85 g of ECR® 385 (a tackifying resin marketed by EXXON CHEMICAL), 0.1 g of IRGANOX® 565 (an antioxidant marketed by CIBA-GEIGY), 3.5 g of SURFADONE® LP300 (N-dodecyl-2-pyrrolidone marketed by BOEHRINGER INGELHEIM), 7.5 g of LAUROGLYCOL® (a mixture of the monoester and diester of propylene glycol and lauric acid, marketed by GATTEFOSSE) and 19.8 g of ethyl acetate are placed in a 250 ml beaker. This mixture is stirred, while being heated at 60° C., until the compounds have completely dissolved. A solution of 1.25 g of norethisterone acetate, previously dissolved in 6.25 g of tetrahydrofuran, is then added. The resulting mixture is stirred for about 30 minutes until it is completely homogeneous. It is left to cool until the bubbles have totally disappeared. The resulting mass is coated onto a siliconized polyester film at a rate of (110±10) g/m² at room temperature (15–20° C.). The coating produced is heated at 50° C. for at least 30 minutes and then transferred to a polyethylene support. The product is cut into shapes of the desired dimensions.

The advantages of the present invention were illustrated by carrying out ex vivo permeation tests on the abdominal skin of male nude mice according to the following protocol:

The amounts of hormones (i.e. steroids) released by a transdermal device with a surface area of 2.54 cm², previously cut out with a hollow punch and deposited on a 3.14 cm² disk of abdominal skin of a male nude mouse, are measured in a static glass cell, thermostated at 37° C., which has a receiving compartment with a volume of 11.5 ml containing a receiving phase made up of an isotonic solution/PEG$_{400}$ mixture (75/25; v/v).

Samples of the receiving solutions are taken at 2, 4, 6, 8, 12, 16, 20 and 24 hours and assayed by liquid chromatography. To allow for the variability of the results associated with the intrinsic permeability of the skin samples, each permeation experiment for a sample of transdermal device is performed on a minimum of 3 to 5 skin samples. The result given is the mean obtained for each device from these experiments.

The following mean skin absorption fluxes were thus obtained for 17-β-estradiol ($F_{ES}$) and/or norethisterone acetate ($F_{NETA}$) in the case of devices 1 to 7:

Device 1: $F_{NETA}$=0.35±0.16 µg/cm²/h

Device 2: $F_{ES}$=0.2±0.07 µg/cm²/h  $F_{NETA}$=0.39±0.1 µg/cm²/h

Device 3: $F_{ES}$=0.61±0.08 µg/cm²/h

Device 4: $F_{ES}$=0.57±0.13 µg/cm²/h  $F_{NETA}$=0.57±0.17 µg/cm²/h

Device 5: $F_{NETA}$=0.5±0.03 µg/cm²/h

Device 6: $F_{NETA}$=0.47±0.05 µg/cm²/h

Device 7: $F_{NETA}$=0.89±0.12 µg/cm²/h

Tables I to V illustrate the reduction in surface area obtained by the systems according to the invention, relative to a comparative system formed of two juxtaposed devices each containing a single active principle, in the case of the simultaneous transdermal delivery of 17-β-estradiol and norethisterone acetate.

Thus Table I compares a system I according to the invention, consisting of devices 4 and 5, with a comparative system Ia, consisting of devices 3 and 5.

Table II compares a system II according to the invention, consisting of devices 2 and 1, with a comparative system IIa, consisting of devices 3 and 1.

Table III compares a system III according to the invention, consisting of devices 4 and 1, with a comparative system IIIa, consisting of devices 3 and 1.

Table IV compares a system IV according to the invention, consisting of devices 4 and 6, with a comparative system IVa, consisting of devices 3 and 6.

Table V compares a system V according to the invention, consisting of devices 4 and 7, with a comparative system Va, consisting of devices 3 and 7.

The abbreviations used in these Tables have the following meanings:

$SD_1$ represents the surface area of the first device, expressed in $cm^2$.

$SD_2$ represents the surface area of the second device, expressed in $cm^2$.

S represents the total surface area of the system formed by the juxtaposition of both devices, expressed in $cm^2$.

G represents the reduction in surface area, expressed as a percentage, for the systems according to the invention (represented by the second line of the Tables) relative to systems formed by the juxtaposition of two devices each containing a single active principle (represented by the first line of the Tables).

The first device contains a mixture of 17-β-estradiol and norethisterone acetate in the case of the systems according to the invention, or 17-β-estradiol only in the case of the comparative systems.

The second device always contains norethisterone acetate only.

TABLE I

|  | $SD_1$ | $SD_2$ | S | G |
|---|---|---|---|---|
| Comparative system Ia | 3.4 | 20.8 | 24.2 |  |
| System I | 3.6 | 16.7 | 20.3 | 16.1 |

TABLE II

|  | $SD_1$ | $SD_2$ | S | G |
|---|---|---|---|---|
| Comparative system IIa | 3.4 | 29.8 | 33.2 |  |
| System II | 10.4 | 18.1 | 28.5 | 14.1 |

TABLE III

|  | $SD_1$ | $SD_2$ | S | G |
|---|---|---|---|---|
| Comparative system IIIa | 3.4 | 29.8 | 33.2 |  |
| System III | 3.6 | 23.8 | 27.4 | 17.3 |

TABLE IV

|  | $SD_1$ | $SD_2$ | S | G |
|---|---|---|---|---|
| Comparative system IVa | 3.4 | 22.2 | 25.6 |  |
| System IV | 3.6 | 17.7 | 21.3 | 16.8 |

TABLE V

|  | $SD_1$ | $SD_2$ | S | G |
|---|---|---|---|---|
| Comparative system Va | 3.4 | 11.7 | 15.1 |  |
| System V | 3.6 | 9.4 | 13 | 13.9 |

In the present case it is desired to deliver the following therapeutically effective doses:

50 μg of 17-β-estradiol per 24 hours, and

250 μg of norethisterone acetate per 24 hours.

If it is desired simultaneously to deliver these two hormones contained in a single device, the difference in skin permeability, i.e. skin absorption flux, between the norethisterone acetate and the 17-β-estradiol must be 5. Now, in practice, such a difference, which is theoretically obtainable although already difficult to achieve as such, proves impossible to obtain if allowance is made for the constraints of stability, comfort and adhesive and cohesive properties required by the marketing of such a device.

Thus devices 2 and 4, which have these good physicochemical properties and offer a good level of comfort, do not make it possible to achieve adjustment of the desired doses.

It is impossible to obtain the desired effective dose of norethisterone acetate without a 2.5-fold and 5-fold increase, respectively, in the doses of 17-β-estradiol delivered. The alternative solution, which uses a system formed of 2 juxtaposed matrix devices, one containing the 17-β-estradiol and the other containing the norethisterone acetate, is less efficient than the solution according to the invention, which affords a reduction in surface area relative to the former by virtue of associating a first matrix device containing a mixture of the two hormones, in which the concentration of norethisterone acetate does not enable the desired dose of 250 μg per 24 hours to be obtained, with a second device containing the norethisterone acetate only, which provides the complementary dose necessary for adjustment to 250 μg per 24 hours.

Thus, for a comparative system Ia in Table I, using device 3 with a skin absorption flux of 0.61 μg/$cm^2$/h, it is necessary to use a device with a surface area of 3.4 $cm^2$ in order to deliver 50 μg of 17-β-estradiol in 24 hours.

Similarly, to deliver 250 μg of norethisterone acetate in 24 hours from device 5 with a skin absorption flux of 0.5 μg/h/$cm^2$, it is necessary to use a device with a surface area of 20.8 $cm^2$. This gives an overall surface area of 24.2 $cm^2$ for a comparative system Ia.

By contrast, for a system I according to the invention, it is found that, using device 4 with skin absorption fluxes of 0.57 μg/h/$cm^2$ for norethisterone acetate and 17-β-estradiol, it is necessary to use a device with a surface area of 3.6 $cm^2$ in order to deliver 50 μg of 17-β-estradiol in 24 hours. This device of 3.6 $cm^2$ will allow the simultaneous delivery of 49.2 μg of norethisterone acetate in 24 hours. 200.8 μg of norethisterone acetate therefore remain to be delivered in order to achieve the desired dose of 250 μg. This amount will be obtained with device 5, which will have a surface area of 16.7 $cm^2$ for a skin absorption flux of 0.5 μg/h/$cm^2$.

The complete system I will therefore have a surface area of 20.3 $cm^2$, representing a 16.1% reduction relative to the comparative system Ia described above, based on devices 3 and 5.

Analysis of Table II similarly shows that a 14.1% reduction in surface area is obtained with a system II according to the invention. This result is very interesting because in this case the flux of 17-β-estradiol (0.2±0.07 μg/h/cm²) of device 2 of the system II according to the invention, containing both the hormones, is much lower than that of device 3 of the comparative system IIa, containing 17-β-estradiol only ($F_{ES}$=0.61 μg/h/cm²), which means that device 2 has to have a very large surface area (10.4 cm²) in the system according to the invention. Despite this, a valuable reduction in surface area is obtained with the system II according to the invention, relative to the comparative system IIa. This result is all the more remarkable because device 2 also has a low flux of norethisterone acetate of 0.39 μg/h/cm², meaning that the amount of norethisterone acetate to be delivered by the complementary device 1 is still large.

It may also be pointed out that, in this case, the flux of norethisterone acetate of device 1, common to both systems, is low: $F_{NETA}$=0.35 μg/h/cm².

It is nevertheless found that, as far as this device 1 is concerned, the system II according to the invention affords a large reduction in surface area relative to the comparative system IIa, namely 18.1 cm² against 29.8 cm², i.e. a 40% reduction.

One of the consequences of this situation is to increase the number of possible formulations which can be used, because even if they have low skin permeation fluxes, this does not necessarily mean that excessively large surface areas have to be used.

In Table V, where, in contrast to the previous case, the flux of norethisterone acetate of device 7, common to both systems, is high (0.89 μg/h/cm²), resulting in a low overall surface area of 15.1 cm² for the comparative system Va (where each device contains a single hormone), a reduction in surface area of the order of 14% is still found for the system V according to the invention.

Results of the same order are obtained with Tables III and IV, where the reductions in surface area are 17.3 and 16.8% respectively.

These two Tables and Table V emphasize yet another advantage of the present invention, namely the use of different kinds of devices for producing the system.

Thus device 4 based on ethylene/vinyl acetate copolymer has been coupled either with device 1 based on the same type of copolymer but with a different formulation (Table III), or with device 6 based on poly(styrene/ethylene/butylene/styrene) block copolymer (Table IV), or with device 7 based on poly(styrene/isoprene/styrene) block copolymer (Table V).

The extended choice of compounds which can be used in the compositions of the devices, and the above-mentioned ability to use devices with low fluxes, facilitate adjustment of the desired dosages of each active principle and therefore considerably widen the possible scope for the development and adaptation to several posologies of comfortable systems of reasonable size for the simultaneous delivery of at least two active principles.

These reductions in surface area of the order of 15 to 20%, exemplified here for estrogen/progestin systems, can obviously be even more advantageous, depending on the permeability of the active principles used.

We claim:

1. A system for the simultaneous transdermal delivery of at least two active principles from at least two juxtaposed devices, said system comprising:
   (a) a first device containing a mixture of all the active principles in which at least one first active principle (A) is present in an amount which enables the effective therapeutic dose to be delivered, and at least one second active principle (B) is present in an amount which is less than that required to deliver the therapeutic dose, and
   (b) one or more additional devices each containing a single active principle (B) selected from those present in the first device and provided in an amount which is less than that required to deliver the effective therapeutic dose, the sum total of the amount in said additional device(s) making up the balance of the effective therapeutic dose of each of the active principles (B) present in the system.

2. The system according to claim 1 wherein the devices of the system are selected from the group consisting of reservoir delivery system and matrix delivery system.

3. The system according to claim 1, wherein the devices of the system are selected from the group consisting of monolayer, multilayer.

4. The system according to claim 1 wherein said system has a single support for all the devices; and wherein each of said devices are associated onto said support by methods selected from the group consisting of sticking onto an adhesive coated support, juxtaposed double coating, and heat sealing onto a single support.

5. The system according to claim 1 wherein each of said devices have an independent support which can be either identical or different.

6. The system according to claim 1 for the delivery of two active principles A and B comprising:
   (i) a first matrix device which is a matrix containing a major amount of the active principle A in an amount which enables the effective therapeutic dose to be delivered, and the active principle B in an amount which is less than that necessary to deliver the effective therapeutic dose;
   (ii) a second matrix device which is a matrix containing a major amount of the active principle B in an amount which makes up the amount present in said first matrix device until its effective therapeutic dose is obtained.

7. The system according to claim 1, wherein the active principles to be delivered simultaneously are selected from the group consisting of estrogen compounds and progestin compounds.

8. The system according to claim 7, wherein the estrogen compound is 17-β-estradiol and the progestin compound is norehisterone acetate.

9. The system according to claim 2, wherein the said system has a single support for all the devices.

10. The system according to claim 3, wherein the said system has a single support for all the devices.

11. The system according to claim 2, wherein each device has an independent support.

12. The system according to claim 3, wherein each device has an independent support.

13. The system according to claim 2, wherein the active principles to be delivered simultaneously are selected from the group consisting of estrogen compounds and progestin compounds.

14. The system according to claim 3, wherein the active principles to be delivered simultaneously are selected from the group consisting of estrogen compounds and progestin compounds.

15. The system according to claim 4, wherein the active principles to be delivered simultaneously are selected from the group consisting of estrogen compounds and progestin compounds.

16. The system according to claim 5, wherein the active principles to be delivered simultaneously are selected from the group consisting of estrogen compounds and progestin compounds.

17. The system according to claim 6, wherein the active principles to be delivered simultaneously are selected from the group consisting of estrogen compounds and progestin compounds.

18. A method for simultaneous transdermal delivery of at least two active principles to a mammal in need of treatment comprising the steps of:
(a) providing a system comprising at least two juxtaposed devices, said system comprising:
 (i) a first device containing a mixture of all the active principles comprising at least one first active principle (A), and at least one second active principle (B); and
 (ii) one or more additional devices each containing a single active principle (B) selected from the active principles present in the first device;
(b) delivering at least two active principles in the first device wherein the first active principle (A) being present in an amount effective to provide the therapeutic dose; and the second active principle (B) being present in an amount less than the required effective therapeutic dose;
c) conducting the delivery of a single active principle (B) in the one or more additional devices being present in an amount which is less than that required to deliver the effective therapeutic dose, said additional device or devices making up the amount of each of the active principle (B) present; and
(d) continuing the delivery steps (b) and (c) until the effective therapeutic dose is reached.

19. The method according to claim 18 wherein the devices of the system are selected from the group consisting of reservoir delivery system and matrix delivery system.

20. The system according to claim 2 wherein the devices are formed by superposition of several matrices or reservoir delivery system, optionally being separated by microporous membranes.

* * * * *